United States Patent
Meribout et al.

(10) Patent No.: US 12,050,191 B2
(45) Date of Patent: Jul. 30, 2024

(54) METHOD FOR ACCELERATING THE DATA ACQUISITION THROUGHPUT OF ELECTRICAL TOMOGRAPHY SYSTEMS

(71) Applicant: Khalifa University of Science and Technology, Abu Dhabi (AE)

(72) Inventors: Mahmoud Meribout, Abu Dhabi (AE); Varun Kumar Tiwari, Abu Dhabi (AE); Khalid Alhammadi, Abu Dhabi (AE); Naji Mohammed Al Sayari, Abu Dhabi (AE); Lyes Khezzar, El Khroub (DZ)

(73) Assignee: Khalifa University of Science and Technology, Abu Dhabi (AE)

( * ) Notice: Subject to any disclaimer, the term of this patent is extended or adjusted under 35 U.S.C. 154(b) by 0 days.

(21) Appl. No.: 18/056,022

(22) Filed: Nov. 16, 2022

(65) Prior Publication Data
US 2024/0167971 A1 May 23, 2024

(51) Int. Cl.
*G01N 27/02* (2006.01)
*A61B 5/0536* (2021.01)
(Continued)

(52) U.S. Cl.
CPC ......... *G01N 27/02* (2013.01); *G01N 33/2823* (2013.01); *G01R 27/28* (2013.01);
(Continued)

(58) Field of Classification Search
CPC .. G01N 27/02; G01N 33/2823; A61B 5/0536; G01R 27/02; G01R 27/28;
(Continued)

(56) References Cited

U.S. PATENT DOCUMENTS

| | | |
|---|---|---|
| 10,371,656 B2 | 8/2019 | Wang et al. |
| 10,921,275 B2 | 2/2021 | Kersey |

(Continued)

OTHER PUBLICATIONS

Maung et al., "Real-time Controlling Particle Distribution in Pneumatic Conveyance by Electrical Capacitance Tomography with Airflow Injection System (ECT-AIS)", Advanced Powder Technology, vol. 31, No. 6, Jun. 2020, pp. 2530-2540.

(Continued)

*Primary Examiner* — Raul J Rios Russo
(74) *Attorney, Agent, or Firm* — Kilpatrick Townsend & Stockton LLP

(57) ABSTRACT

Electrical Tomography (ET) Images of an object can be generated based on features extracted during an excitation cycle. For example, a method described herein can include selecting, from a plurality of electrodes attached to the object, a first pair of electrodes. The method can include exciting the first pair of electrodes during a first excitation cycle. Additionally, the method can include generating an analog signal by performing measurements across remaining pairs of electrodes of the plurality of electrodes during the excitation cycle. The method can include generating the digital signal based on an analog to digital conversion of the analog signal. Further, the method can include extracting, during the excitation cycle, features based on the digital signal. The method can include generating an ET image associated with the object based on the features.

20 Claims, 13 Drawing Sheets

(51) Int. Cl.
| | |
|---|---|
| *G01N 33/28* | (2006.01) |
| *G01R 27/28* | (2006.01) |
| *G01R 27/32* | (2006.01) |
| *H04B 3/46* | (2015.01) |
| *H04B 17/00* | (2015.01) |
| *H04B 17/10* | (2015.01) |

(52) U.S. Cl.
CPC ............ *G01R 27/32* (2013.01); *A61B 5/0536* (2013.01); *H04B 3/46* (2013.01); *H04B 17/0085* (2013.01); *H04B 17/103* (2015.01)

(58) Field of Classification Search
CPC ...... G01R 27/32; H04B 3/46; H04B 17/0085; H04B 17/103
USPC .......................................................... 324/650
See application file for complete search history.

(56) References Cited

U.S. PATENT DOCUMENTS

| | | | |
|---|---|---|---|
| 11,042,982 | B2 | 6/2021 | Liu et al. |
| 2015/0137831 | A1* | 5/2015 | Pluta .................... G01R 33/323 324/647 |
| 2018/0067063 | A1* | 3/2018 | Cherkassky ....... G01R 19/0038 |
| 2018/0374244 | A1* | 12/2018 | Borbás .................... G01R 27/14 |
| 2020/0069206 | A1* | 3/2020 | Zaliasl .................... A61B 5/276 |
| 2021/0003523 | A1* | 1/2021 | Chandak .............. G01N 27/028 |
| 2021/0219863 | A1* | 7/2021 | Wang .................... A61B 5/7235 |

OTHER PUBLICATIONS

Daguerre et al., "A Localization Method for Untethered Small-Scale Robots using Electrical Impedance Tomography", IEEE/ASME Transactions on Mechatronics, vol. 22, No. 5, Available online at: 10.1109/TMECH.2022.3142924, hal-03812921, Dec. 16, 2022, 11 pages.
Lee et al., "Predicting the Force Map of an ERT-Based Tactile Sensor Using Simulation and Deep Networks", IEEE Transactions on Automation Science and Engineering, vol. 20, No. 1, Jan. 2023, 15 pages.
Zhou et al., "A Real-time EIT Imaging System Based on the Split Augmented Lagrangian Shrinkage Algorithm", Measurement, vol. 110, Nov. 2017, pp. 27-42.
Yoshimoto et al., "Influence of Electrode Positions on Performance of Hand Motion Capture Using EIT", IEEE Transactions on Medical Robotics and Bionics, vol. 4, No. 1, Feb. 2022, pp. 285-288.
Lee et al., "Portable Multi-parameter Electrical Impedance Tomography for Sleep Apnea and Hypoventilation Monitoring: Feasibility Study", Physiological Measurement, vol. 39, No. 12, Dec. 21, 2018, 12 pages.
Meribout et al., "A Pipelined Parallel Hardware Architecture for 2-D Real-Time Electrical Capacitance Tomography Imaging Using Interframe Correlation", IEEE Transactions on Very Large-Scale Integration (VLSI) Systems, vol. 25, No. 4, Apr. 2017, pp. 1320-1328.
Meribout et al., "Real-Time Two-Dimensional Imaging of Solid Contaminants in Gas Pipelines Using an Electrical Capacitance Tomography System", IEEE Transactions on Industrial Electronics, vol. 64, No. 5, May 2017, pp. 3989-3996.
Atagi et al., "Real-Time Imaging of Particles Distribution in Centrifugal Particles-Liquid Two-Phase Fields by Wireless Electrical Resistance Tomography (WERT) System", IEEE Access, vol. 7, Jan. 17, 2019, pp. 12705-12713.
Kim et al., "A 1.4-m Ω-Sensitivity 94-dB Dynamic-Range Electrical Impedance Tomography SoC and 48-Channel Hub-SoC for 3-D Lung Ventilation Monitoring System", IEEE Journal of Solid-State Circuits, vol. 52, No. 11, Nov. 2017, pp. 2829-2842.
Yang et al., "A Multi-Frequency Electrical Impedance Tomography System for Real-Time 2D and 3D Imaging", The Review of Scientific Instruments, vol. 88, No. 8, Aug. 23, 2017, pp. 085110-1-085110-12.
Xu et al., "An FPGA-Based Multifrequency EIT System with Reference Signal Measurement", IEEE Transactions on Instrumentation and Measurement, vol. 70, 2021, 10 pages.
Darnajou et al., "High Speed EIT With Multifrequency Excitation Using FPGA and Response Analysis Using FDM", IEEE Sensors Journal, vol. 20, No. 15, Aug. 1, 2020, pp. 8698-8710.
Bai et al., "A Modified Noise Model of Electrical Impedance Tomography System by Considering Colored Noises", IEEE Transactions on Instrumentation and Measurement, vol. 71, Jan. 18, 2022, 10 pages.
Hao et al., "2-D Median Filter-Based Impulsive Noise Reduction in Multifrequency Phase-sensitive Demodulation of Electrical Impedance Tomography", IEEE Transactions on Instrumentation and Measurement, vol. 69, No. 1, Jan. 2020, pp. 54-64.
Takhti et al., "Structured Design Methodology to Achieve a High SNR Electrical Impedance Tomography", IEEE Transactions on Biomedical Circuits and Systems, vol. 13, No. 2, Apr. 2019, pp. 364-375.

* cited by examiner

METHOD FOR ACCELERATING THE DATA ACQUISITION THROUGHPUT OF ELECTRICAL TOMOGRAPHY SYSTEMS

BACKGROUND OF THE INVENTION

Electrical tomography (ET) consists of building an image of a medium by injecting into it either AC electrical current or AC voltage signals, depending on a gross conductance value for the medium. ET can be non-radioactive, non-intrusive, and non-invasive, in addition to providing real-time images of a volume of the medium. ET can be suitable for several applications. For instance, in hospitals, ET can be used for permanently monitoring a patient's breath and cervical activity by placing several electrodes around the chest and the brain, respectively. In oil fields, ET may emerge to be used in some multiphase flow meters (MPFMs) for measuring in real-time the flow rates of oil, water, and gas produced by each well in an oil field. MPFMs can be very valuable devices in upstream oil fields since they significantly contribute to enhance the oil production throughput by shutting down the less effective wells that are connected into a common manifold. For instance, in subsea wells, optimizing oil production is challenging since flow from all the wells can be comingled in a subsea manifold, and thus identifying old wells can be difficult, and techniques, such as techniques that use artificial lifts, may not be employed in this case unless the flow rate of each phase of a multiphase flow is measured. One of the main challenges of using ET systems in certain applications can be a relatively slow image acquisition throughput, which can heavily depend on a number of electrodes included in an ET system.

BRIEF SUMMARY OF THE INVENTION

An ET system can enable an accelerated data acquisition throughput that can be independent of a number of electrodes used in the ET system. For example, an ET system described herein can include an analog to digital converter (ADC) configured to generate a digital signal based on an analog to digital conversion of an analog signal. The ET system can include a controller configured to operate at a frequency at least as high as a sampling clock frequency associated with the ADC. The controller can include a processor and a memory in which instructions executable by the processor is stored for causing the processor to perform operations. The operations can include selecting, from a plurality of electrodes attached to an object, a first pair of electrodes. Additionally, the operations can include exciting the first pair of electrodes during an excitation cycle. The operations can further include generating the analog signal by performing measurements across remaining pairs of electrodes of the plurality of electrodes during the excitation cycle. The operations can include extracting, during the excitation cycle, features based on the digital signal. Additionally, the operations can include generating an ET image associated with the object based on the features.

In another example, a method described herein can include selecting, from a plurality of electrodes attached to an object, a first pair of electrodes. The method can include exciting the first pair of electrodes during an excitation cycle. Additionally, the method can include generating an analog signal by performing measurements across remaining pairs of electrodes of the plurality of electrodes during the excitation cycle. The method can further include generating a digital signal based on an analog to digital conversion of the analog signal. The method can include extracting, during the excitation cycle, features based on the digital signal. Additionally, the method can include generating an ET image associated with the object based on the features.

DETAILED DESCRIPTION OF THE INVENTION

Certain aspects and examples of the present disclosure relate to an ET system that enables an accelerated data acquisition throughput that can be independent of a number of electrodes used in the ET system. The ET system can include a very high-speed analog to digital converter (ADC) to digitalize output analog signals corresponding to all possible pairs of the electrodes within an excitation cycle in a time-multiplexed manner. The pairs of electrodes can be referred to as channels. Feature extraction can be performed for each channel in real-time with the excitation cycle. The electrodes can be attached to an object of interest. An ET image of the object can be constructed based on extracted features.

For example, a peak prediction module may be used to estimate a maximum value of a quantity (e.g., output voltage) for each channel. In some examples, a phase of each output analog signal can be extracted. A data acquisition system associated with the ET system may not require a multiple frequency current source. The data acquisition system can operate without a pass-band filter for different frequencies. The ET system can operate at a throughput of at least 9,000 frames per second when operating an excitation signal from a single frequency current source having at least a 10 kHz frequency and when operating at least 32 electrodes. A use of a multiple frequency current source can increase the throughput to an even higher frame rate.

The ET system can be used in oil well environments, as part of a multiphase flow meter, or to monitor contents of a vessel. The ET system can also be used in medical intensive care units to monitor breathing or brain activity. The ET system can be suitable for use in two-dimensional (2D) or three-dimensional (3D) ET applications.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
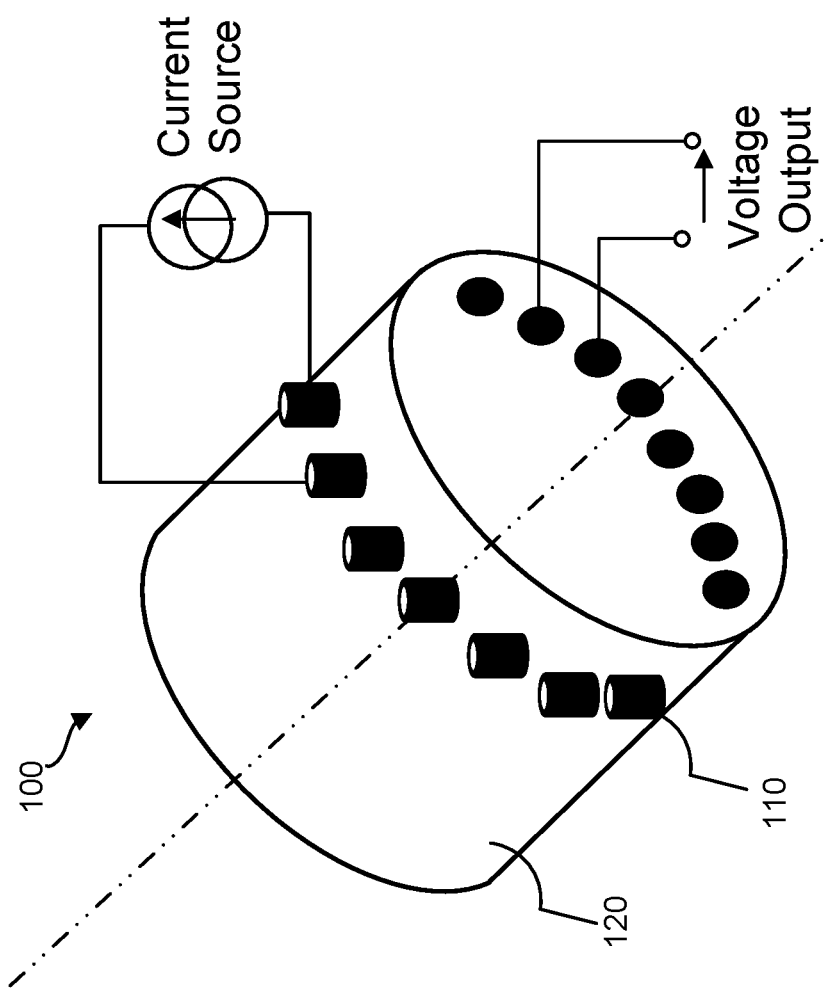
FIG. 1 is a schematic of a perspective view of a sensing module of a two-dimensional (2D) Electrical Tomography (ET) system according to one example of the present application.

FIG. 1 is a schematic of a perspective view of a sensing module 100 of a 2D ET system according to one example of the present application. FIG. 1 depicts a basic configuration for the sensing module 100 of the 2D ET system, where electrodes 110 can be evenly distributed across one single ring around a medium 120 to investigate a target process. Depending on a conductivity of the medium 120, different ET systems can be applied. ET systems can include Electrical Resistance Tomography (ERT), Electrical Impedance Tomography (EIT), Electrical Capacitance Tomography (ECT), and Electromagnetic Tomography (EMT).

For example, in applications (e.g., monitoring multiphase flow featuring high water-cut and low gas void fraction (GVF), brain or breath monitoring, etc.) that include highly conductive media, ERT or Electrical Impedance Tomography EIT can be applied. ERT and EIT can involve a voltage output measurement process. The voltage output measurement process can include applying an excitation AC electric current across two excitation electrodes of the electrodes 110 and recording voltage outputs across pairs of measurement electrodes from the remaining electrodes 110. The pairs of measurement electrodes can be referred to as channels. The frequency of the AC electric current can range from a few kHz up to 10 MHz. The recorded voltage outputs can be used for 2D image reconstruction. Synchronous detection (i.e., phase sensitive detection) can be used to eliminate low frequency drift components in each of the voltage outputs. The voltage output measurement process can be repeated by iteratively applying the excitation AC electric current across all possible pairs of excitation electrodes, which can be time consuming and can lead to a low acquisition throughput. The voltage output measurement process associated with ERT and EIT systems may not be suitable for high-speed processes.

For example, ERT or EIT systems that include 16 electrodes 110 may include 240 (16×15) excitation measurement stages. If a 10 kHz frequency for the excitation AC electric current is used, 24 milliseconds may be needed to acquire voltage output measurements of one single frame. A corresponding frame rate for the voltage output measurements can be 41 frames/second, which may not be a high enough frame rate to satisfy many applications, such as for measuring multiphase flow that can include high velocities.

In applications (e.g., monitoring multiphase fluid flow featuring a low water-cut and high GVF, etc.) that include low conductive media, ECT can be applied. ECT can also involve a voltage output measurement process. Instead of applying an excitation AC electric current across the pair of excitation electrodes, the voltage output measurement process of ECT systems can include applying an excitation AC voltage across a pair of excitation electrodes. Voltage outputs across the pairs of measurement electrodes can be recorded. Each voltage output can be an output analog signal. A frequency of the excitation AC voltage can range from 1 kHz to a few hundred kHz.

Figure 2:
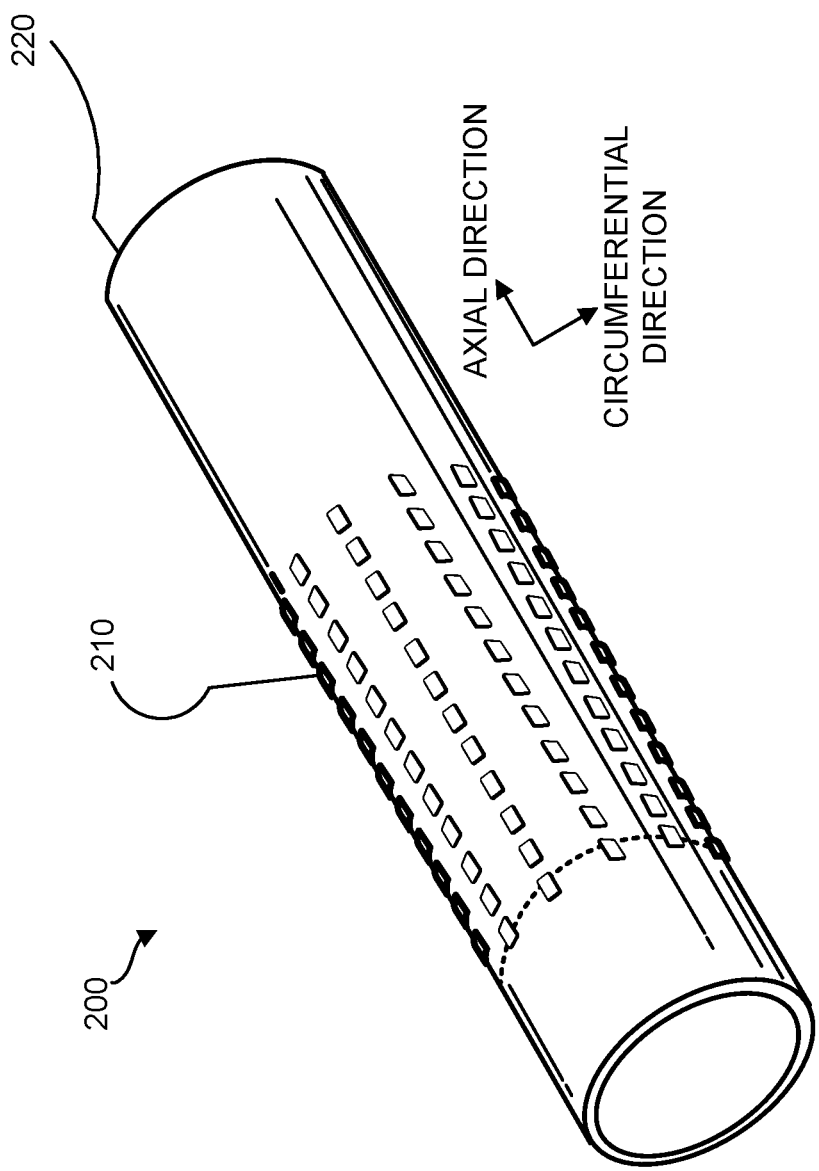
FIG. 2 is a schematic of a perspective view of a sensing module of a three-dimensional (3D) ET system according to one example of the present application.

FIG. 2 is a schematic of a perspective view of a sensing module 200 of a three-dimensional (3D) ET system according to one example of the present application. The sensing module 200 includes an arrangement of electrodes 210 that are arranged into several rings along an axial direction of a pipeline 220. The arrangement of electrodes 210 can be used to build a 3D image or measure the flow rate of a multifluid flow. Like 2D ET systems, 3D ERT or EIT systems can include applying an excitation AC electric current across a pair of excitation electrodes and recording voltage outputs across pairs of measurement electrodes from the other electrodes 210. 3D ET systems can include applying an excitation AC voltage across the pair of the excitation electrodes. Voltage outputs across the pairs of measurement electrodes can be recorded. Each pair of measurement electrodes can form a channel. 3D ET systems can require many more voltage output measurements than corresponding 2D ET systems.

Figure 3:
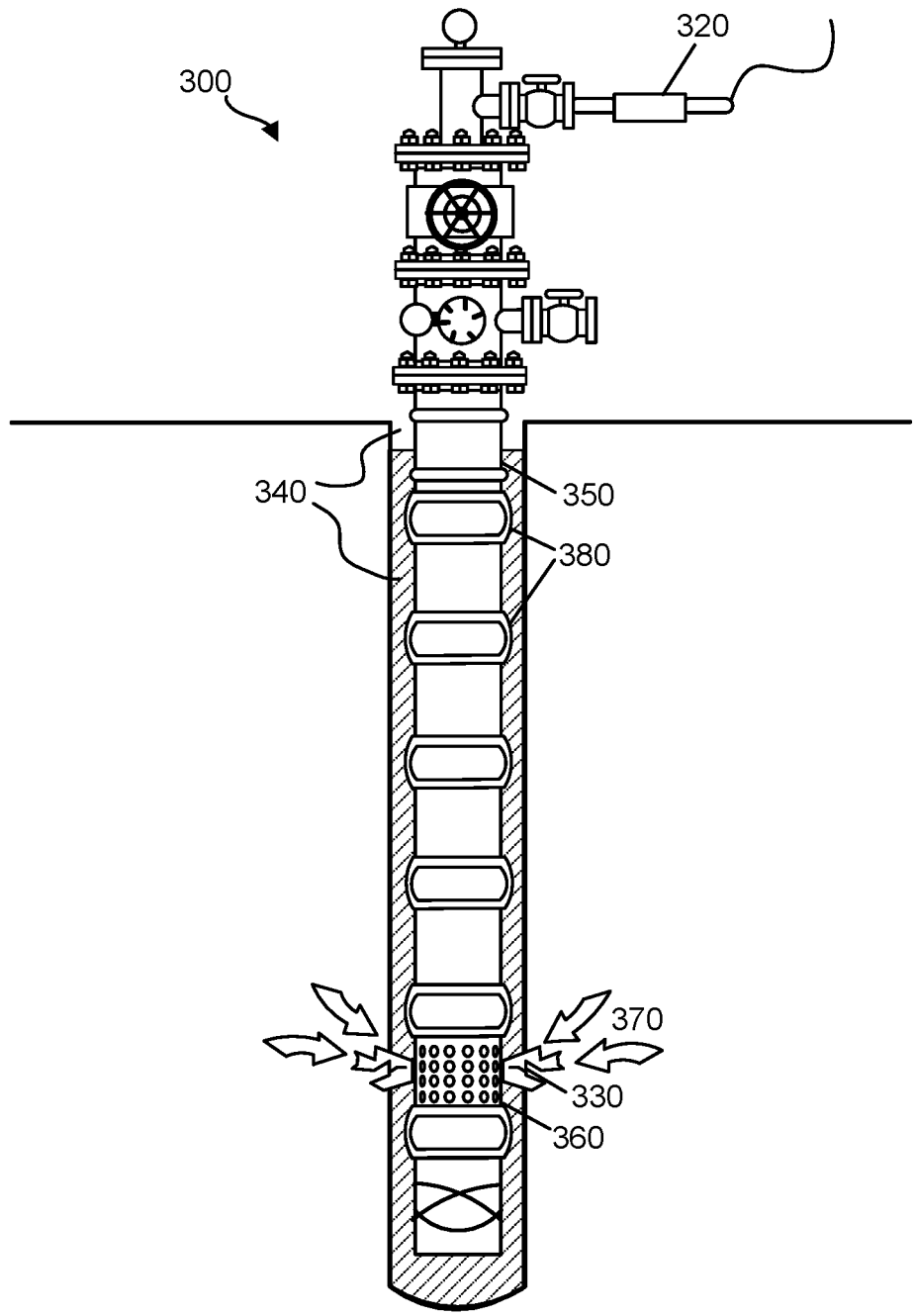
FIG. 3 is a schematic of a cross section of an oil well environment that applies a 2D ET system to measure oil, water, and gas of a multiphase fluid extracted from the oil well according to one example of the present application.

FIG. 3 is a schematic of a cross section of an oil well environment 300 that applies a 2D ET system 320 to measure oil, water, and gas of a multiphase fluid 370 extracted from the oil well environment 300 according to one example of the present application. The 2D ET system 320 can be placed on a well head of the oil well environment 300. In some examples, the 2D ET system 320 can include a sensing module like the sensing module 100 of FIG. 1. Perforations 330 can be provided in one or several positions along a borehole 340 to allow a flow of the multiphase fluid 370 from a surrounding formation into the borehole 340 and then to a surface. A casing string 350 may also include pre-formed openings 360 to allow the flow of the multiphase fluid 370 to reach a wellhead. The casing string 350 can include multiple casing tubulars connected to each other by couplings 380.

Figure 4:
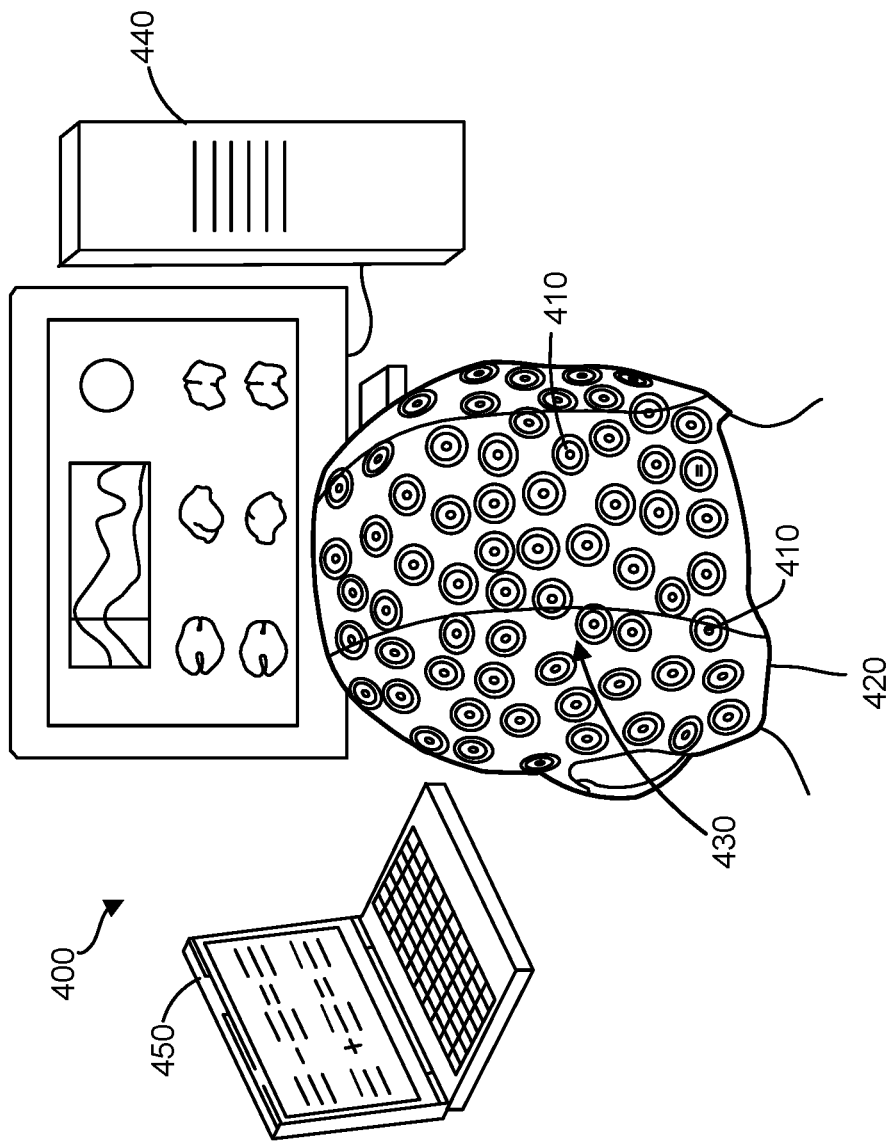
FIG. 4 is a schematic of a 3D ET system used to capture brain activity for a medical patient according to one example of the present application.

FIG. 4 is a schematic of a 3D ET system 400 used to capture brain activity for a medical patient according to one example of the present application. The 3D ET system 400 includes a wearable head cap 420. The wearable head cap 420 includes several electrodes 410 placed within a high-density array 430. Data can be transferred from the electrodes 410 of the wearable head cap 420 to a data acquisition unit 440 and a data visualization unit 450.

Figure 5:
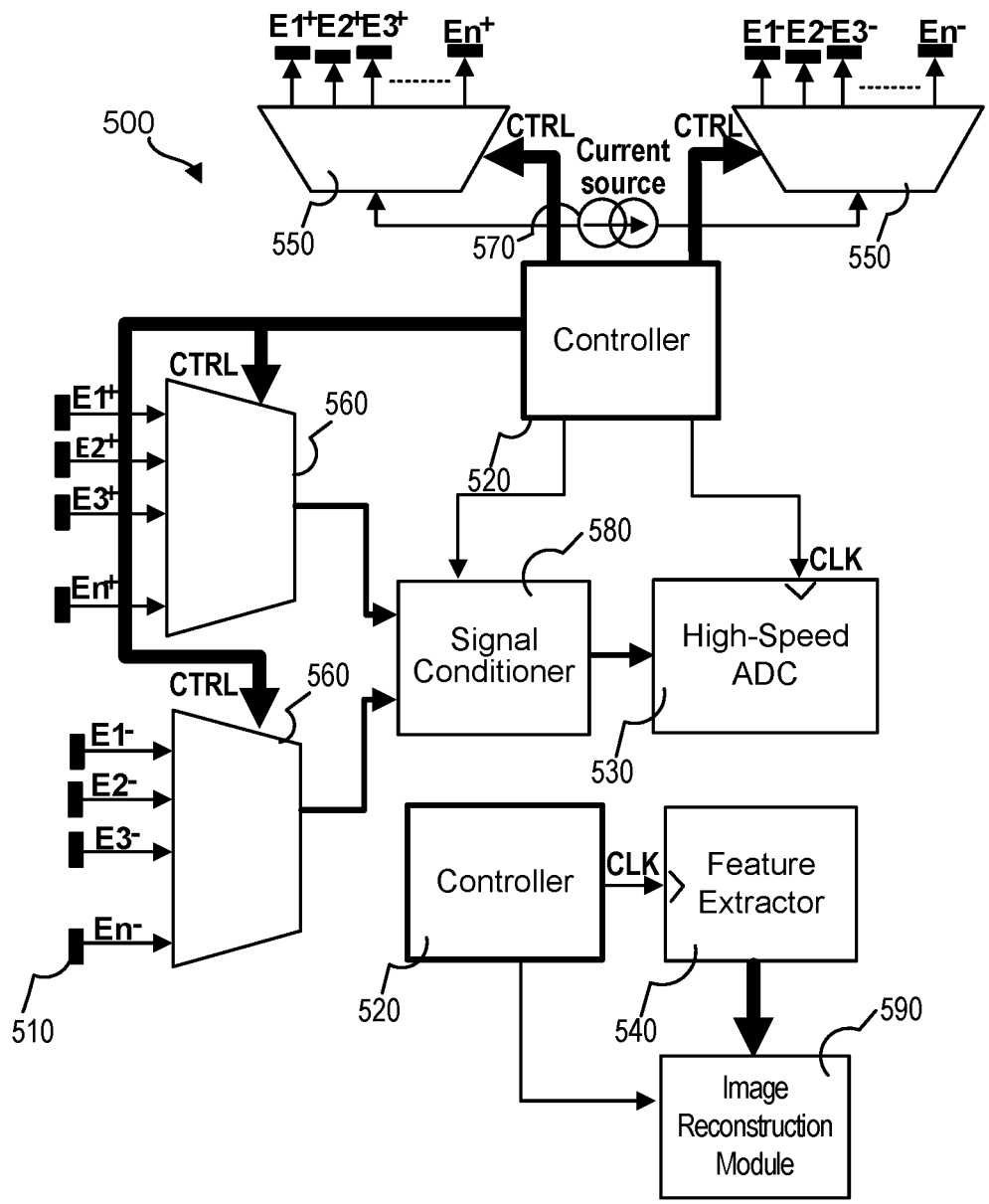
FIG. 5 is a block diagram of a hardware accelerator for an ET system according to one example of the present application.

FIG. 5 is a block diagram of a hardware accelerator 500 for an ET system according to one example of the present application. The hardware accelerator 500 can include a controller 520, a high-speed ADC 530, a signal conditioner 580, at least one demultiplexer module 550, at least one multiplexer module 560, electrodes 510, a feature extractor module 540, a current source 570, and an image reconstruction module 590. A number of the electrodes 510 can be denoted by n.

The controller 520 can operate at a frequency at least as high as a sampling clock frequency associated with a high-speed ADC 530. The controller 520 can capture samples from each channel of the ET system. The controller 520 can be implemented by a microcontroller, a microprocessor, an application-specific integrated circuit (ASIC), or a field programmable gate array (FPGA). The FPGA may be the preferable implementation of the controller 520 because the FGPA can offer low power consumption, a potential for dynamic or static reconfiguration, and higher speed control than Von-Neuman-like architectures.

The controller 520 can instruct the at least one demultiplexer module 550 to select a pair of excitation electrodes from the electrodes 510 to excite with an excitation AC electric current from the current source 570 or an excitation AC voltage. The at least one multiplexer module 560 can be instructed by the controller 520 to select pairs of measurement electrodes from the remaining electrodes 510 to record voltage outputs across the pairs of measurement electrodes. Each pair of measurement electrodes can form a channel. The signal conditioner 580 can include an instrumentation amplifier (IA). The IA can include constraints such as a programmable gain, a very low thermal noise, and very high gain band. The constraints can be provided easily by commercially available, low cost IAs. The feature extractor module 540 can extract features from the voltage output of each channel.

The hardware accelerator 500 depicted in FIG. 5 can be suitable specifically for use in ERT or EIT systems. The hardware accelerator 500 can also be implemented in an ECT system by substituting the current source 570 with a voltage source and by increasing a size of the electrodes 510 to form reasonably measurable capacitance values for the electrodes 510. To implement the hardware accelerator 500 into an EMT system, the electrodes 510 can be in the form of coils.

Figure 6:
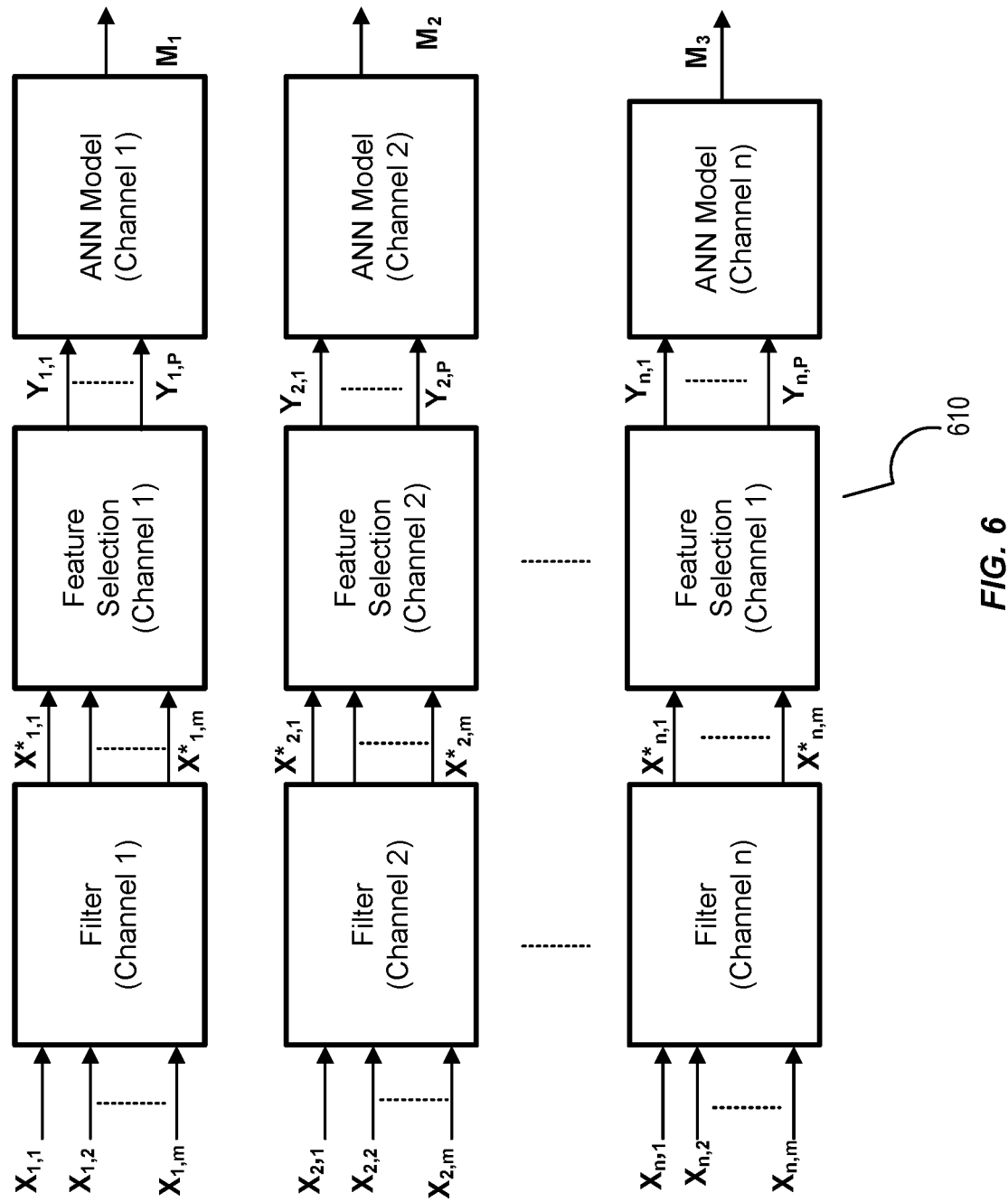
FIG. 6 is a schematic of a data path of a feature extraction aspect of each channel according to one example of the present application.

FIG. 6 is a schematic of data paths of a feature extraction aspect for each channel according to one example of the present application. For each channel i, m samples can be recorded for each excitation cycle. A quantity (denoted X) can be associated with each sample. In a single cycle, the quantity X can have m different values for each channel i: $[X_{i,1}, \ldots, X_{i,m}]$. For each channel i, the quantities $([X_{i,1}, \ldots, X_{i,m}])$ can be processed by a filter to generate at most m filtered quantities: $[X^*_{i,1}, \ldots, X^*_{i,m}]$. For each channel, a feature selection block can select, from the filtered quantities, p input features Y $([Y_{i,1}, \ldots, Y_{i,p}])$ for a regression model. An artificial intelligence model, such as an artificial neural network (ANN), can estimate a final measurement based on the p input features $([Y_{i,1}, \ldots, Y_{i,p}])$. The estimated final measurements $([M_1, \ldots, M_n])$ can be, for example, a maximum peak voltage of the channel signal, a mean value of the signal per excitation cycle, or a phase of the signal corresponding to the channel.

Figure 7:
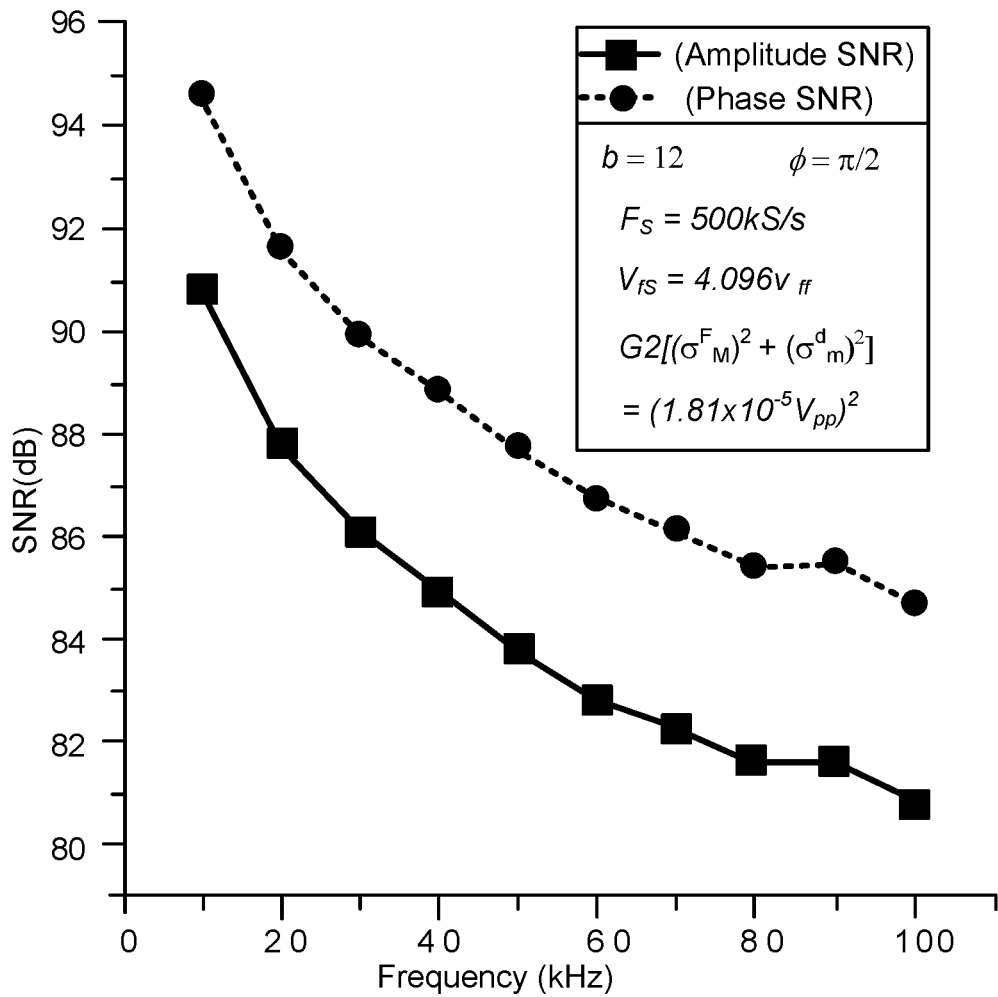
FIG. 7 is a graph depicting a dependence of amplitude signal-to-noise ratio (SNR) and phase SNR on frequency according to one example of the present application.

FIG. 7 is a graph depicting a dependence of amplitude signal-to-noise ratio (SNR) (denoted $SNR_A$) and phase SNR (denoted $SNR_\phi$) on frequency according to one example of the present application. In ET systems, a low value of the SNR can lead to an indistinguishably small impedance change and can lead to poor image resolution for image reconstruction. For example, an acceptable value of the SNR in clinical applications can be above 60 dB. In some applications, a voltage output across some pairs of measurement electrodes (e.g., measurement electrodes with large distance between them) can be extremely weak. Such applications may require a high-resolution ADC.

In order to meet SNR requirements, an ADC 530 and a signal conditioner 580 of a hardware accelerator 500 may need to be carefully designed. A noise signal at an input of the ADC 530 can be caused by high frequency noise of a power supply and can be mitigated by using either low-noise lithium batteries or a high-order high-pass filter. Additionally, the noise signal can be composed of high frequency harmonic noises caused by a non-linearity of analog circuits including an IA circuit and an ADC circuit. The noise signal can also be caused by switching noise caused by a continuous On-Off switching of a control bus of a multiplexer module 560 or a sampling clock of the ADC 530.

The amplitude SNR ($SNR_A$) and phase SNR ($SNR_\phi$) can be computed as follows:

$$(1) \quad SNR_A = 10\log_{10}\left[\frac{\frac{A^2 N}{2}}{\frac{(LSB)^2}{12} + G^2\left[(\sigma_n^r)^2 + (\sigma_n^d)^2\right]}\right]$$

$$(2) \quad SNR_\phi = 10\log_{10}\left[\frac{\frac{A^2 \phi^2 N}{2}}{\frac{(LSB)^2}{12} + G^2\left[(\sigma_n^r)^2 + (\sigma_n^d)^2\right]}\right]$$

$$(3) \quad LSB = \frac{V_{FS}}{2^b}$$

where G represents an IA gain, $V_{FS}$ is a full scale voltage, b is a number of bits of the ADC 530, N is a number of samples converted into digital within one cycle, A is an amplitude of an excitation signal, $\sigma_n^r$ is a variance of thermal noise of the IA, and $\sigma_n^d$ is a variance of thermal noise of a multiplexer/demultiplexer chain. In equations (1) and (2), A and G can be predefined quantities.

Equations (1), (2), and (3) illustrate that there can be four ways to improve the SNR of an ET data acquisition system: by reducing an ADC quantization noise, by reducing the thermal noise of the IA, by reducing the thermal noise of the multiplexer/demultiplexer chain, or by increasing a number of samples/samples or matched filter tap.

FIG. 7 shows that both the $SNR_A$ and $SNR_\phi$ decrease with excitation frequency. An embodiment of the ADC 530 can include 12 bits digital output, a relatively low IA gain, and a low reference voltage. Additionally, the ADC 530 can include a sampling frequency of 150 MHz, which can lead to an acquisition of 3000 samples within one excitation period for a 50 KHz input signal.

Figure 8:
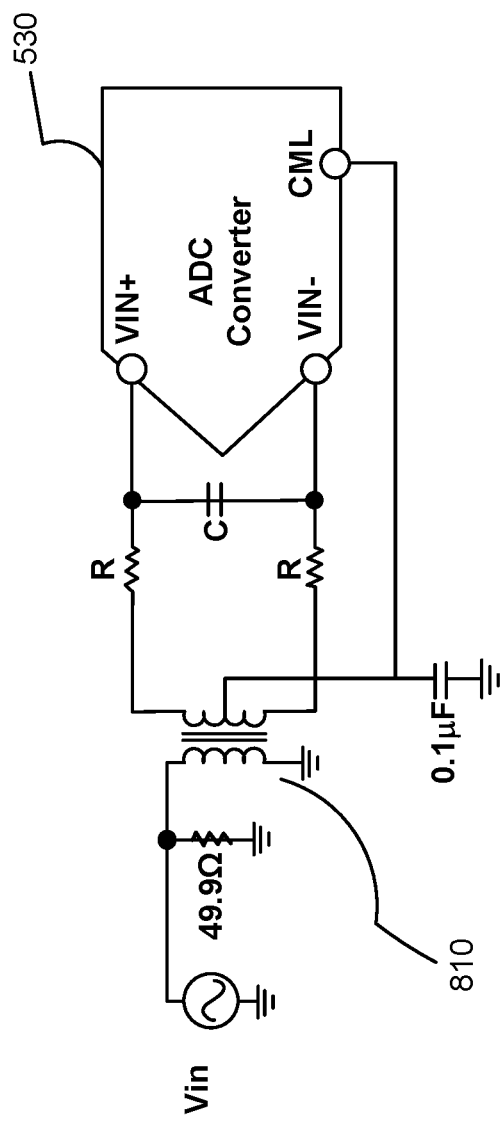
FIG. 8 is a schematic of a differential transformer associated with an analog to digital converter (ADC) for an ET system according to one example of the present application.

FIG. 8 is a schematic of a differential transformer 810 associated with an ADC 530 for an ET system according to one example of the present application. The differential transformer 810 can further increase a SNR for the ET system. A common model level bias output I of current mode logic of the ADC 530 can be connected to a center tap of a secondary winding of the differential transformer 810 to bias an analog input. When selecting parameters associated with the differential transformer 810, signal characteristics should be considered since excessive signal power can cause a core saturation and lead to a distortion.

Figure 9:
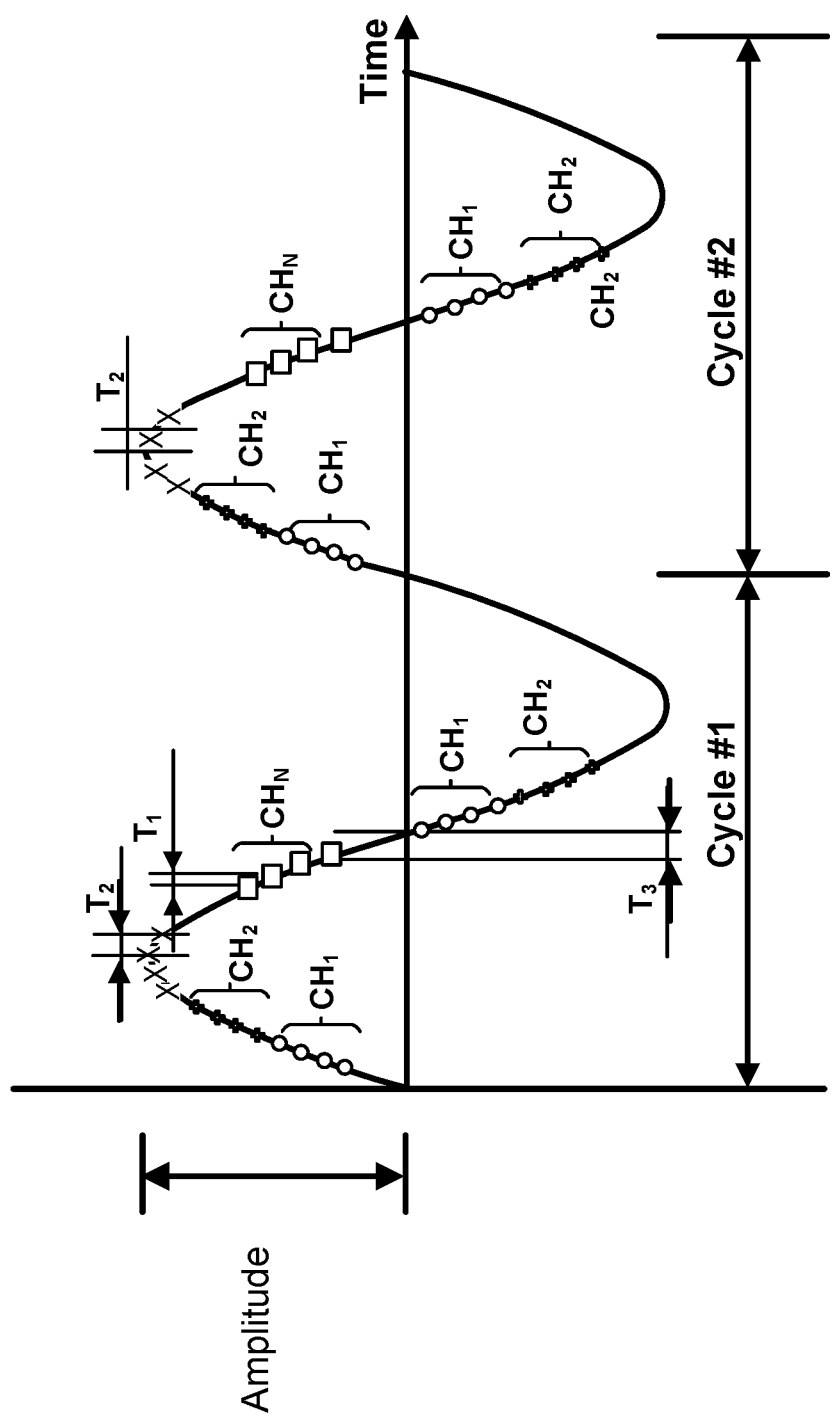
FIG. 9 is a plot of a time dependence of an applied alternating current (AC) signal depicting a first sample capturing sequence according to one example of the present application.

FIG. 9 is a plot of a time dependence of an applied alternating current (AC) signal depicting a first sample capturing sequence according to one example of the present application. The first sample capturing sequence describes a way to extract samples from each channel within an excitation cycle. For each channel of n channels, k samples can be extracted at a sampling rate, $T_1$. A channel switch may require a time delay, $T_2$, which can depend on a switching time of a multiplexer module 560. For example, a 32-channel multiplexer can yield 40 ns and 32 ns switching times when the 32-channel multiplexer operates at 5 Volts and 3.3 Volts, respectively. A sequence of acquiring another stream of data corresponding to the n channels can resume after a time, $T_3$. The time, $T_3$, can be optimized, based on a developed ANN model, to provide a highest possible accuracy for feature extraction at a high acquisition speed. The first sample capturing sequence can lead to reduced switching of the multiplexer module 560. Less switching of the multiplexer module 560 can reduce power consumption and switching noise of the multiplexer module 560.

Figure 10:
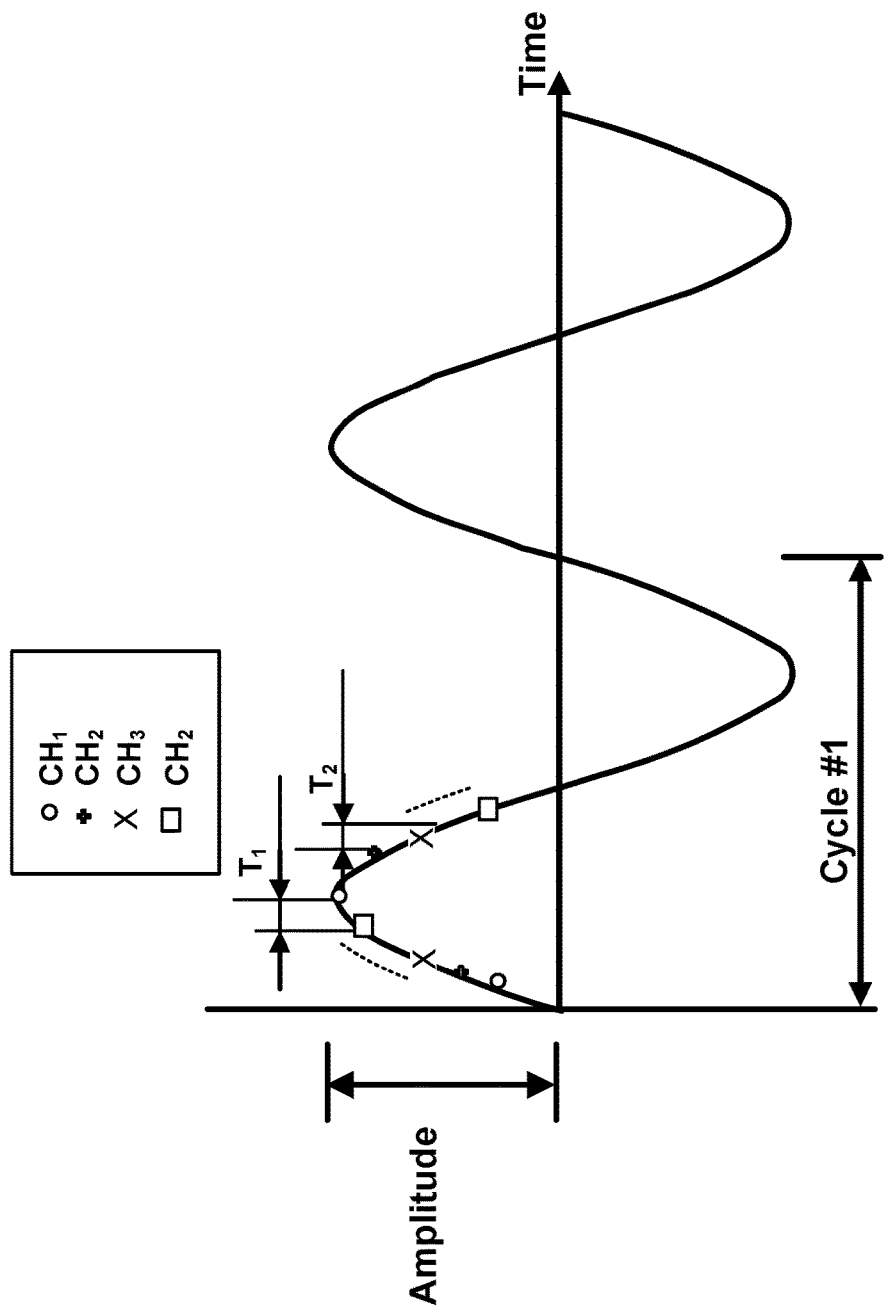
FIG. 10 is a plot of a time dependence of an AC signal depicting an alternative sample capturing sequence according to one example of the present application.

FIG. 10 is a plot of a time dependence of an AC signal depicting an alternative sample capturing sequence according to one example of the present application. The alternative sample capturing sequence describes another way to extract samples from each channel within an excitation cycle. In the alternative sample capturing sequence, switching of a multiplexer module 560 can occur after sampling of a given channel is completed. The alternative sample capturing sequence can optimize an extraction of a number of events that may occur for a given channel within a cycle. But the alternative sample capturing sequence can lead to high-power consumption and higher switching noise than that of a first sample capturing sequence.

Figure 11:
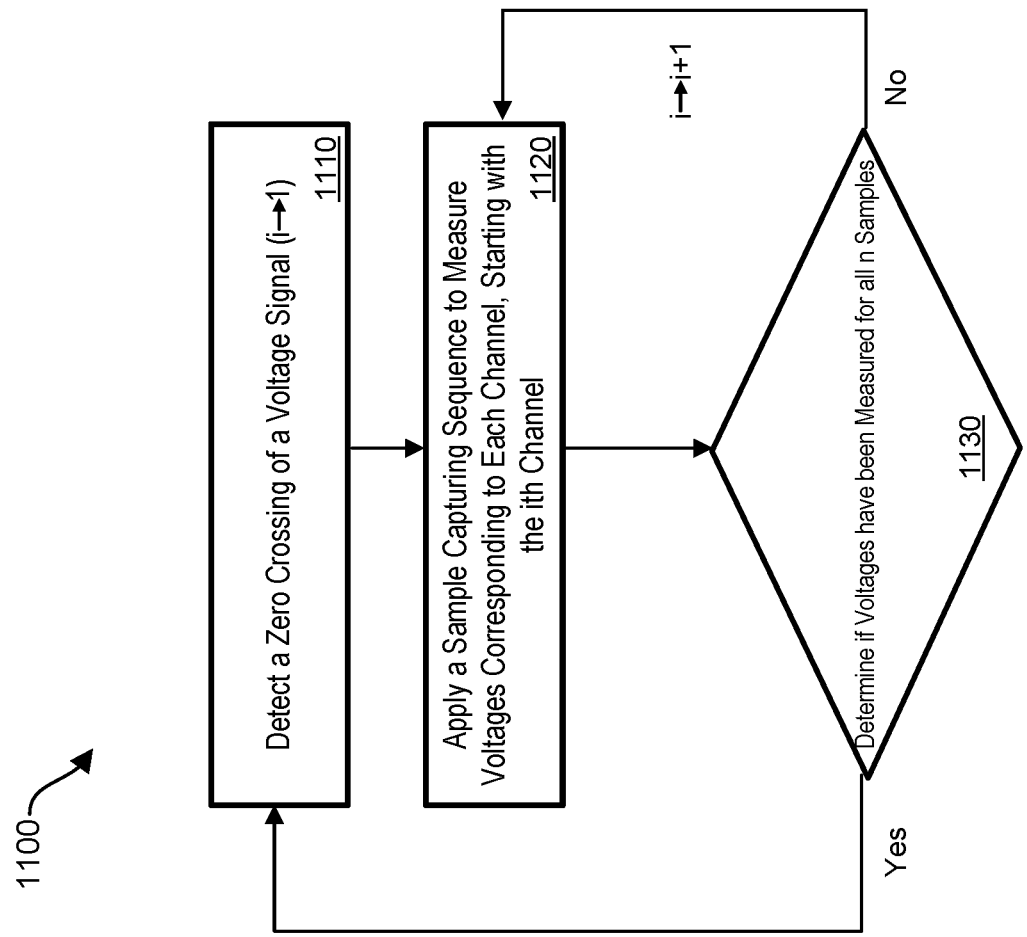
FIG. 11 is a flow chart of a sequencing process for a controller according to one example of the present application.

FIG. 11 is a flow chart of a sequencing process 1100 for a controller 520 according to one example of the present application. Operations of processes may be performed by software, firmware, hardware, or a combination thereof. The operations of the process 1100 start at block 1110.

At block 1110, the sequencing process 1100 involves detecting a zero crossing of a voltage signal. At block 1110, an iterative index i can be set to a value of one. The zero crossing can be detected prior to applying a sampling sequence to ensure that samples are captured with a same phase as a phase captured during a training sequence.

At block 1120, the sequencing process 1100 involves applying a sample capturing sequence to measure voltages corresponding to each channel. The sample capturing sequence can be the first sample capturing sequence depicted in FIG. 9 or the alternative sample capturing sequence depicted in FIG. 10. The voltage measurements can start with the ith channel.

At block 1130, the sequencing process 1100 involves determining if the voltages have been measured for all n channels. The iterative index i can be evaluated at block 1130. If i<n, then voltages have not been measured for all n channels, and the process 1100 can return to block 1120 with the iterative index i converted to i. Otherwise, if i=n, then the voltages have been measured for all n channels and the process 1100 can return to block 1110 and the process 1100 can be repeated.

Figure 12:
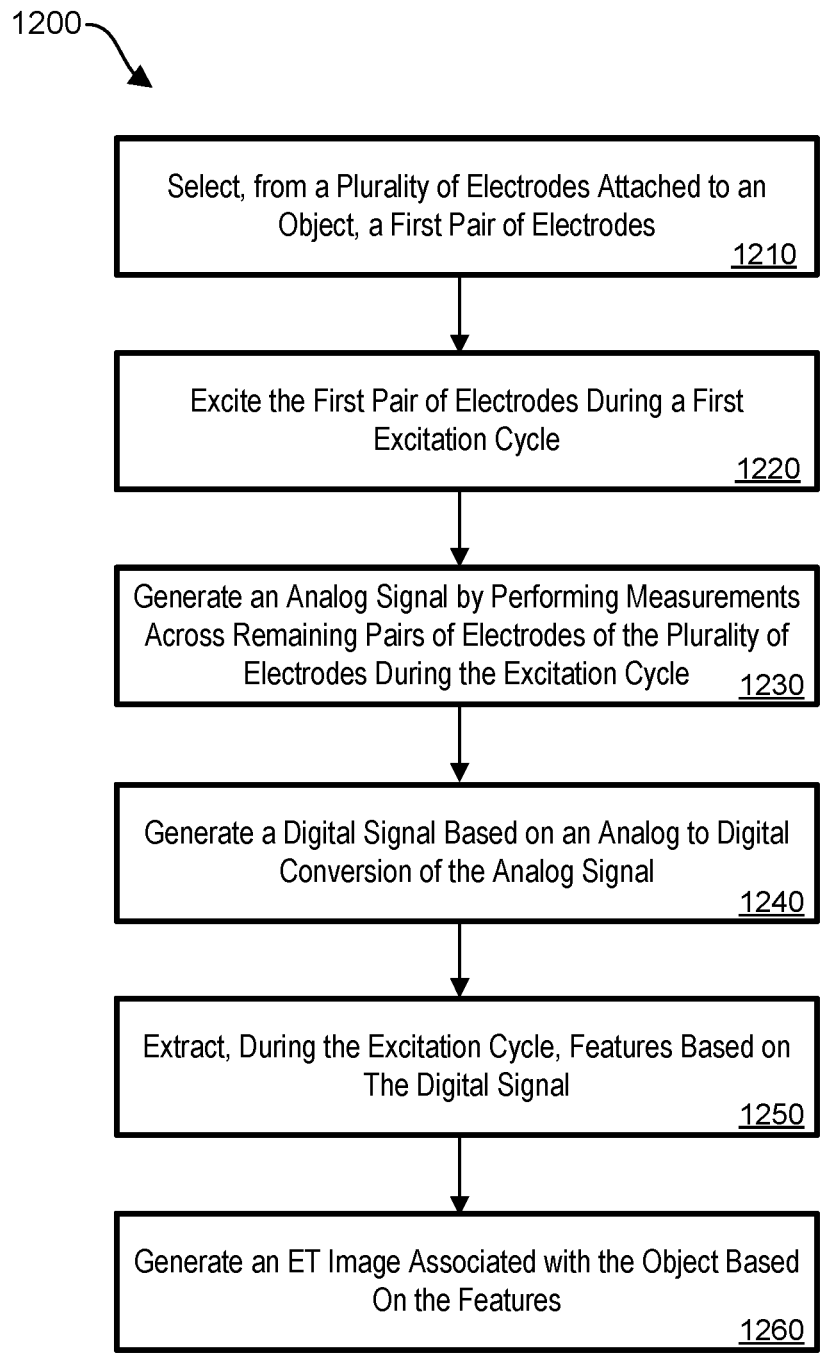
FIG. 12 is a flow chart of a method for generating an image of an object based on features extracted during an excitation cycle.

FIG. 12 is a flow chart of a method 1200 associated with an ET system for generating an image of an object based on features extracted during an excitation cycle. Operations of methods may be performed by software, firmware, hardware, or a combination thereof. The operations of the method 1200 start at block 1210.

At block 1210, the method 1200 involves selecting, from a plurality of electrodes attached to an object, a first pair of electrodes. The first pair of electrodes can be referred to as a pair of excitation electrodes. The first pair of electrodes can be selected by a demultiplexer module 550 controlled by a controller 520. In some examples, the ET system is a 2D ET system and the plurality of electrodes are attached to the object along a line that borders a cross-sectional area. Additionally, the ET system can be a 3D system and the plurality of electrodes are arranged across a surface along a border of a volume.

At block 1220, the method 1200 involves exciting the first pair of electrodes during a first excitation cycle. In some examples, the first pair of electrodes can be excited by an excitation AC electric current, and the ET system can be an ERT system or an EIT system. In other examples, the first pair of electrodes can be excited by an excitation AC voltage and the ET system can be an ECT system.

At block 1230, the method 1200 involves generating an analog signal by performing measurements across remaining pairs of electrodes of the plurality of electrodes during the excitation cycle. The remaining pairs of electrodes can be referred to as pairs of measurement electrodes or channels. Each pair of the remaining pairs of electrodes can be selected by a multiplexer module 560 controlled by the controller 520.

At block 1240, the method 1200 involves generating a digital signal based on an analog to digital conversion of the analog signal. The analog to digital conversion can be performed by a high-speed ADC 530. The ADC 530 can digitalize analog signals corresponding to all remaining pairs of electrodes within the excitation cycle in a time-multiplexed manner.

At block 1250, the method 1200 involves extracting, during the excitation cycle, features based on the digital signal. The features can be extracted from the measurements of the remaining pairs of electrodes. The measurements can be processed by a filter prior to an extraction. In some examples, the features can be inputs for a regression model. An ANN can estimate a final measurement based on the input features. The estimated final measurement can be, for example, a maximum peak voltage of a channel signal, a mean value of the channel signal per excitation cycle, or a phase of the channel signal.

Figure 13:
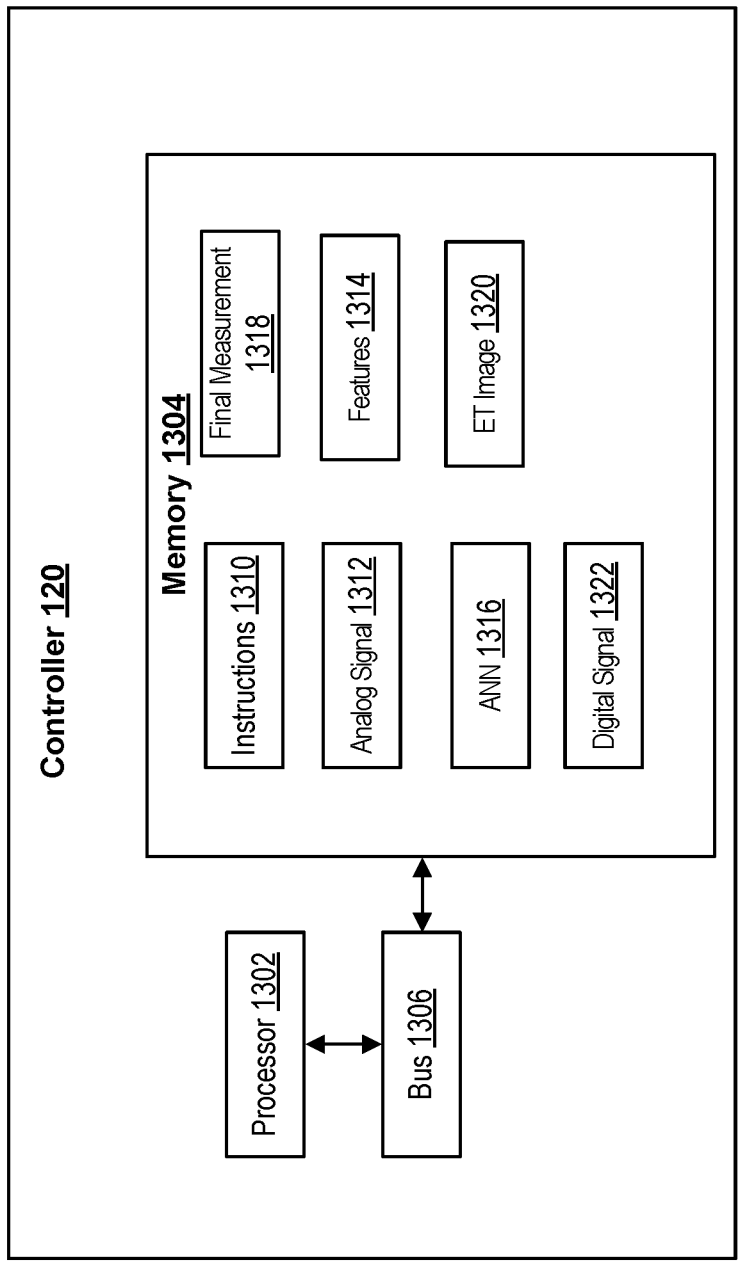
FIG. 13 is a block diagram of a controller for use in an ET system according to one example of the present application.

FIG. 13 is a block diagram of a controller 520 for use in an ET system according to one example of the present application. The components shown in FIG. 13, such as a processor 1302, a memory 1304, a bus 1306, and the like, may be integrated into a single structure such as within the single housing of the controller 520. Alternatively, the components shown in FIG. 13 can be distributed from one another and in electrical communication with each other.

As shown, the controller 520 includes the processor 1302 communicatively coupled to the memory 1304 by the bus 1306. The processor 1302 can include one processor or multiple processors. Non-limiting examples of the processor 1302 include a Field-Programmable Gate Array (FPGA), an application specific integrated circuit (ASIC), a microprocessor, or any combination of these. The processor 1302 can execute instructions 1310 stored in the memory 1304 to perform operations. In some examples, the instructions 1310 can include processor-specific instructions generated by a compiler or an interpreter from code written in any suitable computer-programming language, such as C, C++, C#, or Java.

The memory 1304 can include one memory device or multiple memory devices. The memory 1304 can be non-volatile and may include any type of memory device that retains stored information when powered off. Non-limiting examples of the memory 1304 include electrically erasable and programmable read-only memory (EEPROM), flash memory, or any other type of non-volatile memory. At least some of the memory 1304 can include a non-transitory computer-readable medium from which the processor 1302 can read instructions 1310. The non-transitory computer-readable medium can include electronic, optical, magnetic, or other storage devices capable of providing the processor 1302 with the instructions 1310 or other program code.

Non-limiting examples of the non-transitory computer-readable storage medium include magnetic disk(s), memory chip(s), RAM, an ASIC, or any other medium from which a computer processor can read instructions 1310.

The memory 1304 can further include an analog signal 1312, features 1314, an ANN 1316, a final measurement 1318, a digital signal 1322, and an ET image 1320. The processor 1302 can generate the analog signal 1312 by performing a measurement across a pair of electrodes. The analog signal 1312 can be converted into the digital signal 1322 by an ADC 530. The processor 1302 can extract the features 1314 based on the digital signal 1322. The ET image 1320 associated with an object can be generated by the processor 1302 based on the features 1314. In some examples, the features 1314 can be input into the ANN 1316. The ANN can estimate a final measurement 1318 based on the features 1314. In some examples, the ET image 1320 can be generated based at least in part on the final measurement 1318.

In some examples, the controller 520 can implement the process shown in FIG. 11 or FIG. 12 for effectuating some aspects of the present disclosure. Other examples can involve more operations, fewer operations, different operations, or a different order of the operations shown in FIG. 11 or FIG. 12.

In the preceding description, various embodiments have been described. For purposes of explanation, specific configurations and details have been set forth to provide a thorough understanding of the embodiments. However, it will also be apparent to one skilled in the art that the embodiments may be practiced without the specific details. Furthermore, well-known features may have been omitted or simplified in order not to obscure the embodiment being described.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes and workflows disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the description to provide a thorough understanding of the embodiments. However, it will be understood that the embodiments may be practiced without these specific details. For example, specific computational models, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method implemented by an Electrical Tomography (ET) system, the method comprising:
   selecting, from a plurality of electrodes attached to an object, a first pair of electrodes;
   exciting the first pair of electrodes during an excitation cycle;
   generating an analog signal by performing measurements across remaining pairs of electrodes of the plurality of electrodes during the excitation cycle;
   generating, by an analog to digital converter (ADC), a digital signal based on an analog to digital conversion of the analog signal;
   extracting, during the excitation cycle, features based on the digital signal; and
   generating an ET image associated with the object based on the features.

2. The method of claim 1, wherein exciting the first pair of electrodes comprises exciting the first pair of electrodes by an excitation AC electric current, and wherein the ET system comprises an Electrical Resistance Tomography (ERT) system or an Electrical Impedance Tomography (EIT) system.

3. The method of claim 1, wherein exciting the first pair of electrodes comprises exciting the first pair of electrodes by an excitation AC voltage, and wherein the ET system comprises an Electrical Capacitance Tomography (ECT) system.

4. The method of claim 1, wherein the plurality of electrodes comprises at least thirty-two electrodes, wherein exciting the first pair of electrodes comprises exciting the first pair of electrodes with an excitation signal having at least a 10 kHz frequency.

5. The method of claim 1, wherein extracting the features is performed at a sampling rate of at least 9,000 frames per second by using either a single or multiple frequency current source.

6. The method of claim 1, wherein the ET system comprises a two-dimensional ET system or a three-dimensional ET system.

7. The method of claim 1, wherein the ET image is generated based at least in part on a final measurement and the method further comprising:
   inputting the features into an artificial neural network (ANN); and
   estimating, using the ANN, the final measurement.

8. An Electrical Tomography (ET) system comprising:
   an analog to digital converter (ADC) configured to generate a digital signal based on an analog to digital conversion of an analog signal; and a controller configured to operate at a frequency at least as high as a sampling clock frequency associated with the ADC, the controller comprising:

a processor; and a memory in which instructions executable by the processor are stored for causing the processor to perform operations comprising:

selecting, from a plurality of electrodes attached to an object, a first pair of electrodes;

exciting the first pair of electrodes during an excitation cycle;

generating the analog signal by performing measurements across remaining pairs of electrodes of the plurality of electrodes during the excitation cycle;

initiating a generation, by the ADC, of the digital signal based on the analog to digital conversion of the analog signal;

extracting, during the excitation cycle, features based on the digital signal; and generating an ET image associated with the object based on the features.

9. The ET system of claim 8, wherein the excitation cycle is an electric current excitation cycle that uses an electric current signal, wherein each remaining pair of electrodes forms a channel, and wherein the controller is further configured to estimate, during the electric current excitation cycle, a maximal value of the electric current signal per channel, and wherein the ET image is generated based on estimated maximal values.

10. The ET system of claim 8, wherein the excitation cycle is an electric current excitation cycle that uses an electric current signal, wherein each remaining pair of electrodes forms a channel, and wherein the controller is further configured to determine, during the electric current excitation cycle, a phase of the electric current signal per channel, and wherein the ET image is generated based on determined phases.

11. The ET system of claim 8, further comprising:

a demultiplexer module controllable by the controller and configured to select the first pair of electrodes; and a multiplexer module controllable by the controller and configured to switch between the remaining pairs of electrodes.

12. The ET system of claim 11, further comprising:

a current source coupled with the demultiplexer module; and a signal conditioner coupled with the multiplexer module, the controller, and the ADC.

13. The ET system of claim 8, wherein each remaining pair of electrodes forms a channel, and wherein the operations further comprise:

extracting, for each channel "i," "m" samples;

associating a quantity "X" with each sample such that the quantity "X" has "m" values "$[X_{i,1}, \ldots, X_{i,m}]$" for each channel "i;" and generating, for each channel "i," m" filtered quantities "$[X^*_{i,1}, \ldots, X^*_{i,m}]$" based on a filter.

14. The ET system of claim 13, wherein the operations further comprise:

selecting, from the filtered quantities, "p" input features "$([Y_{i,1}, \ldots, Y_{i,p}])$;" and generating an input to a model based on the "p" input features "$([Y_{i,1}, \ldots, Y_{i,p}])$," wherein the ET image is generated based on an output of the model in response to the input.

15. The ET system of claim 14, wherein the model comprises an artificial neural network (ANN) configured to estimate a final measurement "$([M_1, \ldots, M_n])$" based on the "p" input features "$([Y_{i,1}, \ldots, Y_{i,p}])$," wherein the ET image is generated based on the final measurement "$([M_1, \ldots, M_n])$," and wherein the final measurement "$([M_1, \ldots, M_n])$" includes at least one of a maximum peak voltage of a channel signal corresponding to a channel, a mean value of the signal, or a phase of the signal.

16. A non-transitory computer-readable storage medium within an Electrical Tomography (ET) system having program code that is executable by a processor to cause a controller to perform operations, the operations comprising:

selecting, from a plurality of electrodes attached to an object, a first pair of electrodes;

exciting the first pair of electrodes during an excitation cycle;

generating an analog signal by performing measurements across remaining pairs of electrodes of the plurality of electrodes during the excitation cycle;

initiating a generation, by an analog to digital converter (ADC), of a digital signal based on an analog to digital conversion of the analog signal;

extracting, during the excitation cycle, features based on the digital signal; and generating an ET image associated with the object based on the features.

17. The non-transitory computer-readable storage medium of claim 16, wherein the operations further comprise reducing an ADC quantization noise.

18. The non-transitory computer-readable storage medium of claim 16, wherein the operations further comprise reducing a thermal noise of a signal conditioner coupled with the ADC.

19. The non-transitory computer-readable storage medium of claim 16, wherein the first pair is selected via a demultiplexer, wherein a remaining pair is selected via a multiplexer, and wherein the operations further comprise reducing a thermal noise of at least one of the multiplexer or the demultiplexer.

20. The non-transitory computer-readable storage medium of claim 16, wherein each remaining pair of electrodes forms a channel, and wherein the operations further comprise:

detecting a zero crossing of a voltage signal measured across a remaining pair of electrodes;

apply a sample capturing sequence to measure voltages corresponding to each channel; and determining that voltages have been measured for all channels, wherein the digital signal is generated based on the voltages.

* * * * *